United States Patent [19]  [11] 4,312,880
Draber et al.  [45] Jan. 26, 1982

[54] FUNGICIDAL IMIDAZOLYL-ENOL ETHERS

[75] Inventors: Wilfried Draber, Wuppertal; Karl H. Büchel, Burscheid; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 170,276

[22] Filed: Jul. 17, 1980

[30] Foreign Application Priority Data

Aug. 4, 1979 [DE] Fed. Rep. of Germany ....... 2931665

[51] Int. Cl.³ .................. A01N 43/50; C07D 233/56; A01N 59/06; A01N 59/20
[52] U.S. Cl. ................................ 424/273 R; 424/245; 548/101; 548/341
[58] Field of Search ................ 548/341, 101; 424/245, 424/273 R

[56] References Cited

U.S. PATENT DOCUMENTS 4,067,989  1/1978  Shephard et al. ............... 548/341
4,213,990  7/1980  Frick et al. ..................... 548/341
4,233,311 11/1980  Kramer et al. .................. 548/341
4,235,620 11/1980  Lewis et al. .................... 548/341
4,246,020  1/1981  Shephard et al. ................ 548/101

Primary Examiner—John M. Ford
Assistant Examiner—Natalia Harkaway
Attorney, Agent, or Firm—Sprung, Felfe, Horn, Lynch & Kramer

[57] ABSTRACT

Imidazolyl-enol ethers of the formula

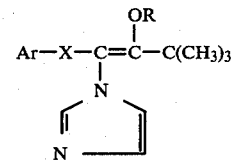

in which
Ar is an optionally substituted aryl radical,
R is an alkyl group, and
X is an oxygen atom or a methylene radial,
or acid or metal salt addition products thereof which possess fungicidal properties.

7 Claims, No Drawings

FUNGICIDAL IMIDAZOLYL-ENOL ETHERS

The present invention relates to certain new imidazolyl-enol ethers, to a process for their production and to their use as fungicides.

It has already been disclosed that imidazolyl ethers, such as, for example, substituted 3,3-dimethyl-1-(imidazol-1-yl)-1-phenoxy-2-(R-oxy)-butanes, have good fungicidal properties (see U.S. Ser. No. 900,401, filed Apr. 26, 1978.) However, the action of these compounds is not always completely satisfactory, especially when low amounts and concentrations are applied.

The present invention now provides, as new compounds, the imidazolyl-enol ethers of the general formula

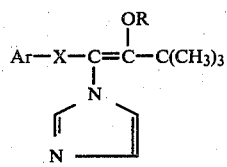

in which
  Ar represents an optionally substituted aryl radical,
  R represents an alkyl group and
  X represents an oxygen atom or a methylene radical,
and acid salt and metal salt addition compounds thereof.

The compounds of the formula (I) according to the invention exist in the form of the geometric isomers E (trans) and Z (cis). In the E,Z nomenclature, the substituents on the double bond are arranged in decreasing priority in accordance with the Cahn-Ingold-Prelog rule. If the preferred substituents are on the same side of the double bond, the compound has the Z configuration (derived from zusammen (together)), and if they are on the opposite side, the compound has the E configuration (derived from entgegen (opposite)). Both the individual isomers and the mixtures are claimed according to the invention.

The new imidazolyl-enol ethers of the present invention have powerful fungicidal properties. Surprisingly, the compounds according to the invention exhibit a considerably more powerful action than the substituted 3.3-dimethyl-1-(imidazol-1-yl)-1-phenoxy-2-(R-oxy)-butanes, which are known from the state of the art and are closely related compounds chemically and from the point of view of their action. The substances according to the invention thus represent an enrichment of the art.

Preferably preferred imidazolyl-enol ethers according to the present invention are those in which Ar represents an aryl radical which has 6 to 10 carbon atoms (preferably a phenyl or naphthyl radical, and which is optionally monosubstituted or polysubstituted by identical or different substituents, preferred substituents being: halogen; alkyl with 1 to 6 (preferably 1 to 4) carbon atoms; alkoxy with 1 to 4 (preferably 1 or 2) carbon atoms; halogenoalkyl with 1 to 4 carbon atoms and 1 to 5 halogen atoms (preferably with up to 2 carbon atoms and up three identical or different halogen atoms), halogen atoms being, preferably, fluorine and chlorine); nitro; cyano; and phenyl which is optionally substituted by halogen (preferably chlorine), R represents a straight-chain or branched alkyl group with 1 to 4 carbon atoms and X has the meaning indicated above.

Very particularly preferred imidazolyl-enol ethers of the formula (I) are those in which Ar represents a phenyl radical which is optionally monosubstituted or disubstituted by identical or different substituents selected from fluorine, chlorine, bromine, iodine, methyl, ethyl, isopropyl, trifluoromethyl, nitro, phenyl and chlorophenyl; R represents a methyl, ethyl, isopropyl, isobutyl or tert.-butyl group; and X has the meaning indicated above.

The following compounds of the general formula (I) may be mentioned specifically, in addition to the compounds mentioned in the preparative examples:

$$Ar-X-\underset{\underset{\underset{N}{\Big[}}{N}}{\overset{\overset{OR}{|}}{C}}=\overset{|}{C}-C(CH_3)_3 \qquad (I)$$

| Ar | X | R |
|---|---|---|
| Cl—⌬— | O | CH₃ |
| Cl—⌬— | O | i-C₃H₇ |
| Cl—⌬— | O | i-C₄H₉ |
| Cl—⌬— | CH₂ | CH₃ |
| Cl—⌬— | CH₂ | C₂H₅ |
| Cl—⌬— | CH₂ | i-C₃H₇ |
| Cl—⌬— | CH₂ | i-C₄H₉ |
| Cl—⌬—⌬— | CH₂ | CH₃ |
| Cl—⌬—⌬— | CH₂ | C₂H₅ |
| Cl—⌬—Cl | O | CH₃ |
| Cl—⌬—Cl | O | C₂H₅ |
| Cl—⌬—Cl | CH₂ | CH₃ |
| Cl—⌬—Cl | CH₂ | C₂H₅ |
| F—⌬— | O | CH₃ |
| F—⌬— | O | C₂H₅ |
| F—⌬— | CH₂ | CH₃ |
| F—⌬— | CH₂ | C₂H₅ |
| Cl—⌬—CH₃ | O | CH₃ |

-continued

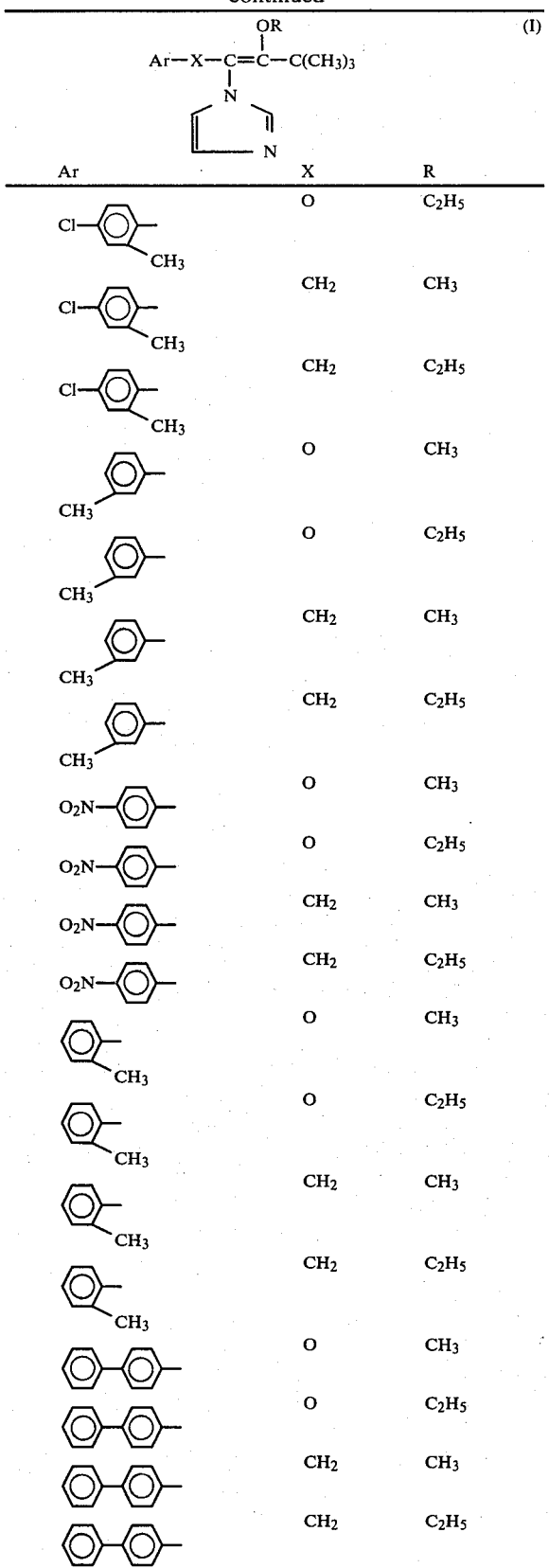

According to the present invention there is further provided a process for the production of a compound of the present invention in which an imidazolyl-ketone of the general formula

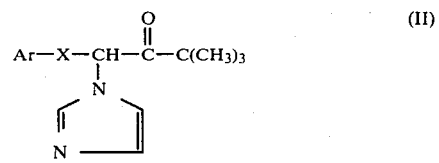

in which

Ar and X have the meaning indicated above, is reacted with an alkyl sulphate or halide in the presence of a base and in the presence of an organic diluent, or in an aqueous-organic two-phase system in the presence of a phase transfer catalyst, and the product is converted, if desired, into an acid salt or a metal salt addition compound thereof.

If, for example, 1-(4-chlorophenoxy)-3,3-dimethyl-1-(imidazol-1-yl)-butan-2-one and dimethyl sulphate are used as starting substances, the course of the reaction for the preparation of compounds of the invention is illustrated by the following equation:

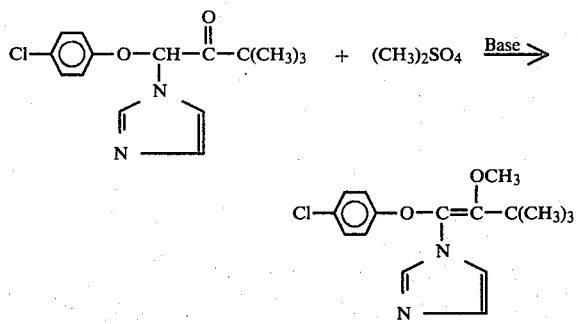

Particularly preferred imidazolyl ketones to be used as starting substances in carrying out the process according to the invention are those in which Ar and X represent those radicals which have already been mentioned for these substituents in connection with the preferred and particularly preferred compounds of the present invention.

The imidazolyl ketones of the formula (II) are known (see DE-AS (German Published Specification) No. 2,105,490 and DE-OS (German Published Specification) No. 2,638,470), and they can be obtained by the processes indicated in these specifications, for example by reacting corresponding halogenoketones with imidazole in the presence of a diluent and in the presence of an acid-binding agent.

The alkyl sulphates and halides also required as starting substances for the process according to the invention are generally known compounds of organic chemistry. Examples which may be mentioned are: dimethyl sulphate, diethyl sulphate, methyl bromide, methyl iodide, ethyl bromide, ethyl iodide, isopropyl iodide and isobutyl iodide.

Possible diluents for the reaction according to the invention are inert organic solvents. These include, preferably, aromatic hydrocarbons, such as benzene, toluene or xylene; halogenated hydrocarbons, such as methylene chloride, carbon tetrachloride, chloroform or chlorobenzene; esters, such as ethyl acetate; formamides, such as dimethylformamide; and dimethylsulphoxide.

The reaction according to the invention may be carried out in the presence of a base. All the customary organic and, in particular, inorganic bases can be employed here, such as, preferably, alkali metal hydroxides or alkali metal carbonates, sodium hydroxide and potassium hydroxide.

The reaction temperatures can be varied within a substantial range in carrying out the process according to the invention. In general, the reaction is carried out between 0° and 100° C., preferably between 20° and 80° C.

In carrying out the process according to the invention, 1 to 2 moles of alkyl sulphate or halide are preferably employed per mole of imidazolyl ketone of the formula (II). The compounds of the formula (I) are thereby obtained in the form of the geometric isomer mixtures. Isolation of the individual geometric isomers is effected by customary methods, such as, for example, on the basis of different solubility, by salt formation, by Craig distribution or by chromatography separation processes, or by a combination of these methods. The structure is allocated unambiguously on the basis of the $^1$H-NMR data, in particular using shift reagents.

In a preferred embodiment, the reaction according to the invention is carried out in a two-phase system, such as, aqueous sodium hydroxide solution or potassium hydroxide solution/toluene or methylene chloride, if appropriate with the addition of 0.1 to 1 mole of a phase transfer catalyst (per mole of imidazolyl ketone of formula (II)) such as ammonium compounds or phosphonium compounds, benzyl-dodecyl-dimethyl-ammonium chloride and triethylbenzyl-ammonium chloride (see also the preparative examples).

The compounds of the formula (I) which can be prepared according to the invention can be converted into acid addition salts or metal salt complexes.

The following acids can preferably be used for the preparation of physiologically acceptable acid addition salts of the compounds of the formula (I): hydrogen halide acids (such as, hydrobromic acid and in particular hydrochloric acid), phosphoric acid, nitric acid, sulphuric acid, monofunctional and bifunctional carboxylic acids and hydrocarboxylic acids (such as, acetic acid, maleic acid, succinic acid, fumaric acid, tartaric acid, citric acid, salicyclic acid, sorbic acid and lactic acid), and sulphonic acids (such as toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII can preferably be used for the preparation of metal salt complexes of the compounds of the formula (I), examples of metals which may be mentioned being copper, zinc, manganese, magnesium tin, iron and nickel.

Possible anions of the salts are those which are derived, preferably, from the following acids: hydrogen halide acids, such as hydrochloric acid and hydrobromic acid, and furthermore phosphoric acid, nitric acid and sulphuric acid.

The metal salt complexes of compounds of the formula (I) can be obtained in a simple manner by customary processes, thus, for example, by dissolving the metal salt in alcohol, for example ethanol, and adding the solution to the compound of the formula (I). Metal salt complexes can be purified in a known manner, for example by filtration, isolation and, if appropriate, by recrystallization.

The active compounds according to the invention exhibit a powerful microbial action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as powdery mildew of cereal and cereal rust; Uromyces species, such as the bean rust causative organism (*Uromyces phaseoli*); and Erysiphe species, such as the powdery mildew of cucumber causative organism (*Erysiphe cichoracearum*).

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents, can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLE

EXAMPLE 1

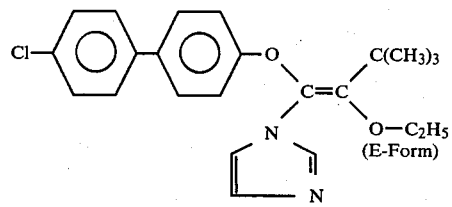

6 g of potassium hydroxide, dissolved in a little water, were added dropwise to 36.85 g (0.1 mole) of 1-(4'-chloro-4-biphenyloxy)-3,3-dimethyl-1-(imidazol-1-yl)-butan-2-one in 50 ml of dimethylsulphoxide. The mixture was subsequently stirred for a short time and 16 g (0.11 mole) of diethyl sulphate were then added dropwise. During this addition, the temperature of the reaction mixture was kept at about 40° C., and thereafter was kept at 80° C. for about ½ hour. The mixture was allowed to cool, water was added and the crystalline precipitate was filtered off and recrystallized from petroleum ether. 22 g (50% of theory) of (E)-1-(4'-chloro-4-biphenylyloxy)-3,3-dimethyl-2-ethoxy-1-(imidazol-1-yl)-butene-1 of melting point 112°–113° C. were obtained.

The following compounds of the general formula $$Ar-X-\underset{\underset{\underset{N}{\Big|}}{N}}{C}=\underset{}{C}-C(CH_3)_3 \quad (I)$$

could be obtained in a corresponding manner:

TABLE 2

| Compound No. | Ar | X | R | Melting point (°C.) |
|---|---|---|---|---|
| 2 | Cl—⟨◯⟩— | O | $C_2H_5$ | 94–95 (E-Form) |
| 3 | Cl—⟨◯⟩—⟨◯⟩— | O | $CH_3$ | 139–42 (E-Form) |

The fungicidal activity of the compounds of this invention is illustrated by the following examples wherein the compounds according to the present invention are each identified by the number (given in brackets) from Example 1.

The known comparison compounds are identified as follows:

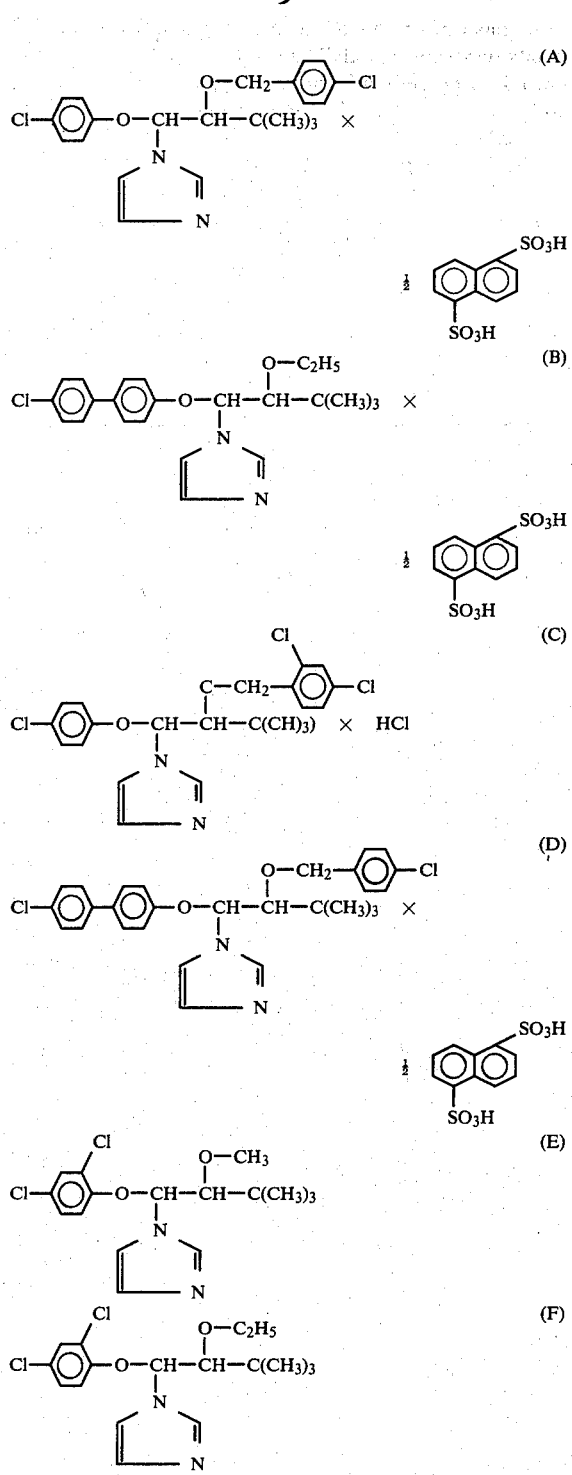

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21°–22° C. and 80–90% atmospheric humidity, the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The test results are as follows:

TABLE 3

| Shoot treatment test/powdery mildew of cereal/protective | | |
|---|---|---|
| Active compounds | Active compound concentration in the spray liquor in % by weight | Infection in % of the untreated control |
| (A) | 0.025 | 48.6 |
| (B) | 0.025 | 60.0 |
| (2) | 0.025 | 0.0 |
| (1) | 0.025 | 23.8 |
| (3) | 0.025 | 0.0 |

EXAMPLE 3

Shoot treatment test/cereal rust/protective (leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier, and 975 parts by weight of water were added. The concentrate was diluted with water to the desired final concentration in the spray liquor.

To test for protective activity, single-leaved young wheat plants of the Michigan Amber variety were inoculated with a uredospore suspension of *Puccinia recondita* in 0.1% strength aqueous agar. After the spore suspension has dried on, the wheat plants were sprayed with the preparation of active compound until dew-moist and were placed, for incubation, in a greenhouse for 24 hours at about 20° C. and 100% atmospheric humidity.

After 10 days' dwell time of the plants at a temperature of 20° C. and 80–90% atmospheric humidity, the occurrence of rust pustules on the plants were evaluated. The degree of infection was expressed as a percentage of the infection of the untreated control plants. 0% denoted no infection and 100% denoted the same degree of infection as in the case of the untreated control. The more active the compound, the lower was the rust infection.

The test results are as follows:

EXAMPLE 2

Shoot treatment test/powdery mildew of cereal/protective (leaf-destructive mycosis)

To produce a suitable preparation of active compound 0.25 part by weight of active compound was taken up in 25 parts by weight of dimethylformamide and 0.06 part by weight of emulsifier (alkylaryl polyglycol ether), and 975 parts by weight of water were added. The concentrate was diluted with water to the desired final concentration of the spray liquor.

TABLE 4

| Shoot treatment est/cereal rust/protective | | |
|---|---|---|
| Active compound | Active compound concentration in the spray liquor in % by weight | Infection in % of the untreated control |
| (C) | 0.025 | 100 |
| (D) | 0.025 | 65.0 |
| (2) | 0.025 | 37.5 |
| (1) | 0.025 | 0.0 |

TABLE 4-continued

Shoot treatment est/cereal rust/protective

| Active compound | Active compound concentration in the spray liquor in % by weight | Infection in % of the untreated control |
|---|---|---|
| (3) | 0.025 | 14.4 |

EXAMPLE 4

Erysiphe test (cucumbers)/protective
Solvent: 4.7 parts by weight of acetone
Emulsifier: 0.3 part by weight of alkylaryl polyglycol ether
Water: 95.0 parts by weight The amount of active compound required for the desired concentration of active compound in the spray liquid was mixed with the stated amount of solvent, and the concentrate was diluted with the stated amount of water which contained the stated additions.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23° to 24° C. and at a relative atmospheric humidity of about 75%.

After 12 days, the infection of the cucumber plants were determined. The assessment data were converted to percent infection. 0% denoted no infection and 100% meant that the plants were totally infected.

The test results are as follows:

TABLE 5

Erysiphe test (cucumber)/protective

| Active compound | Infection in % at an active compound concentration of 0.0001% |
|---|---|
| (E) | 37 |
| (1) | 29 |

EXAMPLE 5

Uromyces test (bean rust)/protective
Solvent: 4.7 parts by weight of acetone
Emulsifier: 0.3 part by weight of alkylaryl polyglycol ether
Water: 95.0 parts by weight The amount of the active compound required for the desired concentration of the active compound in the spray liquid was mixed with the stated amount of solvent, and the concentrate was diluted with the stated amount of water which contained the stated additions.

Young bean plants in the 2-leaf stage were sprayed with the spray liquid until dripping wet. The plants remained in a greenhouse for 24 hours at 20°-22° C. and at a relative atmospheric humidity of 70% in order to dry. They were then inoculated with an aqueous uredospore suspension of the bean rust causative organism (*Uromyces phaseoli*) and incubated for 24 hours in a dark humidity chamber at 20°-22° C. and 100. relative atmospheric humidity.

The plants were then set up in a greenhouse under intensive illumination for 9 days at 20°-22° C. and at a relative atmospheric humidity of 70-80%.

10 days after the inoculation, the infection of the plants was determined. The assessement data were converted to percent infection. 0% denoted no infection and 100% denoted that the plants were completely infected.

The test results are as follows:

TABLE 6

Uromyces test/protective

| Active compound | Infection in % at an active compound concentration of: 0.001% |
|---|---|
| (D) | 100 |
| (F) | 75 |
| (1) | 9 |
| (2) | 62 |

It will be understood that the instant specification and examples are set forth by way of illustration and not limitation, and that various modifications and changes may be made without departing from the spirit and scope of the present invention.

We claim:

1. An imidazolyl-enol ether of the formula

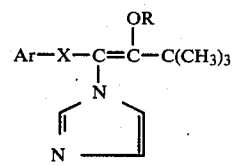

in which
Ar is a phenyl or naphthyl radical which is optionally substituted by halogen, alkyl with 1 to 6 carbon atoms, alkoxy with 1 to 4 carbon atoms, halogenoalkyl with 1 to 4 carbon atoms and 1 to 5 halogen atoms, nitro, cyano, phenyl and/or halophenyl,
R is an alkyl group with 1 to 4 carbon atoms, and
X is an oxygen atom or a methylene radical, or an addition product thereof with a physiologically acceptable acid selected from the group consisting of a hydrogen halide acid, phosphoric acid, nitric acid, sulphuric acid, a monofunctional or bifunctional carboxylic acid or hydroxycarboxylic acid, or a sulphonic acid, or with a metal salt in which the metal is copper, zinc, manganese, magnesium, tin, iron or nickel and the anion is derived from hydrochloric, hydrobromic, phosphoric, nitric or sulphuric acid.

2. A compound according to claim 1, wherein such compound is 1-(4'-chloro-4-biphenylyloxy)-3,3-dimethyl-2-ethoxy-1-(imidazol-1-yl)-butene-1 of the formula

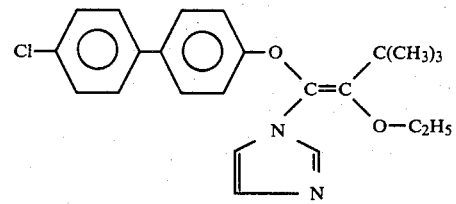

3. A compound according to claim 1, wherein such compound is 1-(4-chlorophenoxy)-3,3-dimethyl-2-ethoxy-1-(imidazol-1-yl)-butene-1 of the formula 4. A compound according to claim 1, wherein such compound is 1-(4'-chloro-4-biphenylyloxy)-3,3-dimethyl-2-methoxy-1-(imidazol-1-yl)-butene-1 of the formula

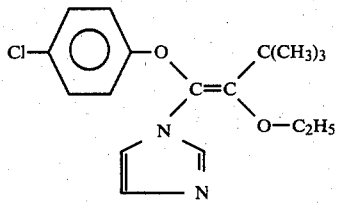

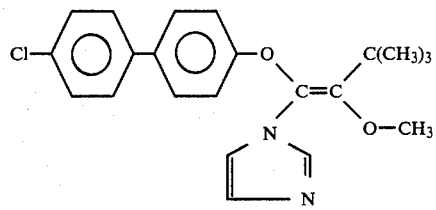

5. A plant fungicidal composition comprising as active ingredient a plant fungicidally effective amount of a compound or addition product thereof according to claim 1 in admixture with a diluent.

6. A method of combating phytopathogenic fungi comprising applying to the fungi, or to a habitat thereof, a plant fungicidally effective amount of a compound or addition product thereof according to claim 1.

7. The method according to claim 6, wherein said compound is
  1-(4'-chloro-4-biphenylyloxy)-3,3-dimethyl-2-ethoxy-1-(imidazol-1-yl)-butene-1,
  1-(4-chlorophenoxy)-3,3-dimethyl-2-ethoxy-1-(imidazol-1-yl)-butene-1, or
  1-(4'-chloro-4-biphenylyloxy)-3,3-dimethyl-2-methoxy-1-(imidazol-1-yl)-butene-1.

* * * * *